US011045281B2

(12) United States Patent
Tsai et al.

(10) Patent No.: US 11,045,281 B2
(45) Date of Patent: Jun. 29, 2021

(54) DIGITAL ORTHODONTIC SETUP USING A PRESCRIBED IDEAL ARCH FORM

(71) Applicant: Ormco Corporation, Orange, CA (US)

(72) Inventors: Evan Yifeng Tsai, Rancho Cucamonga, CA (US); Ian Kitching, Rancho Cucamonga, CA (US)

(73) Assignee: Ormco Corporation, Orange, CA (US)

( * ) Notice: Subject to any disclaimer, the term of this patent is extended or adjusted under 35 U.S.C. 154(b) by 981 days.

(21) Appl. No.: 15/493,970

(22) Filed: Apr. 21, 2017

(65) Prior Publication Data

US 2017/0304023 A1 Oct. 26, 2017

Related U.S. Application Data

(60) Provisional application No. 62/326,446, filed on Apr. 22, 2016.

(51) Int. Cl.
*A61C 7/00* (2006.01)
*G16H 50/50* (2018.01)
(Continued)

(52) U.S. Cl.
CPC ............. *A61C 7/002* (2013.01); *G16H 20/30* (2018.01); *G16H 50/50* (2018.01); *G16H 70/20* (2018.01); *G16H 40/67* (2018.01)

(58) Field of Classification Search
CPC combination set(s) only.
See application file for complete search history.

(56) References Cited

U.S. PATENT DOCUMENTS 6,846,179 B2   1/2005  Chapouland et al.
8,126,726 B2   2/2012  Matov et al.
(Continued)

FOREIGN PATENT DOCUMENTS

WO   2000069358 A1   11/2000
WO   2011089470 A1   7/2011

OTHER PUBLICATIONS

Alan C. Lin, et al., "Integration of 3D CAD, Reverse Engineering and Rapid Prototyping in Fabrication of Invisible Tooth Aligner," Proceeding of the 2005 IEEE International Conference on Mechatronics pp. 647-651 (Year: 2005).*
Bolton, Wayne A., "Disharmoney in Tooth Size and Its Relation to the Analysis and Treatment of Malocclusion", The Angle Orthodontist, vol. 28, Issue 3, Jul. 1958, pp. 113-130.

* cited by examiner

*Primary Examiner* — Rehana Perveen
*Assistant Examiner* — Steven W Crabb
(74) *Attorney, Agent, or Firm* — Wood Herron & Evans LLP

(57) ABSTRACT

The invention generally relates to methods, systems, and computer program products for digital orthodontic setup using a prescribed ideal arch form. The invention may include an imaging system, an orthodontic device production system, and an orthodontic treatment system interconnected by way of a network. The orthodontic treatment system may facilitate manipulating one or more reference teeth into a position by the dental practitioner. The orthodontic treatment system may further facilitate selection of an ideal unit-less arch form and scaling of the ideal unit-less arch form into a scaled ideal arch form to fit the reference teeth. After the selected ideal unit-less arch form is scaled to fit the reference teeth, the remaining teeth are positioned with respect to the scaled ideal arch form, either manually by a dental practitioner or automatically by an alignment algorithm.

17 Claims, 10 Drawing Sheets

(51) Int. Cl.
*G16H 20/30* (2018.01)
*G16H 70/20* (2018.01)
*G16H 40/67* (2018.01)

(56) References Cited

U.S. PATENT DOCUMENTS

| | | |
|---|---|---|
| 2003/0105611 A1 | 6/2003 | Sachdeva |
| 2011/0269097 A1* | 11/2011 | Sporbert ............... A61C 9/0046 433/24 |
| 2013/0282351 A1 | 10/2013 | Tank |
| 2015/0056576 A1 | 2/2015 | Nikolskiy et al. |

DIGITAL ORTHODONTIC SETUP USING A PRESCRIBED IDEAL ARCH FORM

CROSS-REFERENCE TO RELATED APPLICATION

This application claims the benefit of U.S. Provisional Patent Application Ser. No. 62/326,446 filed on Apr. 22, 2016, the disclosure of which is expressly incorporated by reference herein in its entirety.

TECHNICAL FIELD

The invention relates generally to orthodontic treatment and, more particularly, to orthodontic treatment methods and systems for using an arch form.

BACKGROUND

Orthodontics is a specialty of dentistry that is concerned with improvement of the general appearance of a patient's teeth and also the correction of malocclusions, crookedness, and other flaws of the teeth. Orthodontic braces are devices that are placed on a patient's teeth by a dental practitioner. Often, such orthodontic braces are periodically adjusted by the dental practitioner to help align and straighten the teeth. Orthodontic aligners are removable devices that are placed in a patient's mouth to adjust and straighten the teeth and are periodically replaced to progress the treatment. Treatment by the dental practitioner may help in repositioning the teeth to correct flaws and improve the general appearance of the patient.

The dental practitioner may take impressions and capture X-ray images of the teeth and the surrounding skeletal structure. The dental practitioner may also use cone beam computed tomography (CBCT), which involves the use of a rotating CBCT scanner, combined with a digital computer, to obtain images of the teeth and surrounding bone structure, soft tissue, muscle, blood vessels, etc. An intra-oral imaging system may be used as a diagnostic tool to allow a dental practitioner to see the inside of a patient's mouth and display the topographical characteristics of teeth on a display monitor. Certain three-dimensional (3D) intra-oral imagers may be comprised of an intra-oral camera with a light source. The 3D intra-oral imager may be inserted into the oral cavity of a patient by a dental practitioner. After insertion of the intra-oral imager into the oral cavity, the dental practitioner may capture images of visible parts of the teeth and the gingiva.

A dental practitioner may write a prescription based on an analysis of the impression of the teeth, the X-ray images, the CBCT images, intra-oral imagery, etc. While performing the analysis, the dental practitioner may use software for cephalometric analysis of the CBCT images, the panoramic X-rays, and the cephalometric X-rays. The prescription written by the dental practitioner may be used to manufacture orthodontic braces or aligners. In a traditional orthodontic brace, wires interact with brackets to move teeth to a desired position. Periodic adjustments are needed to the orthodontic brace for satisfactory completion of treatment. Other methods that use clear removable plastic aligners that level and align teeth may also be used by certain dental practitioners.

As described above, digital imagery is widely used in dental diagnosis and treatment planning. Three-dimensional models that represent teeth may be used for performing various operations related to dentistry, such as the design of braces or aligners. Such models of teeth may be manipulated within a three-dimensional graphics system for providing various types of display for use by a dental practitioner. The models may comprise three-dimensional digital representations of a patient's teeth and may also be referred to as virtual models (as opposed to physical models that may be cast in plaster). Software platforms may allow dental practitioners to modify virtual models (i.e., three-dimensional digital representations) of a patient's teeth, where the virtual models are suspended in space on display screens.

The field of orthodontics is developed around the fundamental belief that there always exists an ideal arrangement of teeth which offers the most functional, hygienic, and aesthetic benefits to the patient, despite individual anatomical variations among people. This ideal arch form, however, assumes considerably different shapes and definitions among various schools of thought. In addition, clinical observations suggest that it should be among a dental practitioner's treatment goals to move the teeth as little as possible, while keeping the movements "natural". This reduces distortions and stress in the periodontal tissues to the minimum, thus preventing diseases from occurring years after the treatment.

As orthodontic diagnosis and treatment planning have moved into the digital realm in recent years, improved methods, systems, and computer program products are needed to facilitate a setup of the patient's teeth in digital three-dimensional space, whereby movement of the teeth is minimal and most natural and individualized to an ideal arch form.

SUMMARY

The present invention overcomes the foregoing and other shortcomings and drawbacks of orthodontic treatment planning with methods and systems heretofore known. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, a method for making a prescribed arch form based on a model of a set of teeth includes using an algorithm to select an ideal arch form. The method further includes scaling the selected ideal arch form to fit at least one tooth in the model and repositioning at least one other tooth in the model to align it with the scaled arch form so as to form a prescribed setup. The method further includes transmitting information sufficient to manufacture an orthodontic appliance in accordance with the prescribed setup.

In one embodiment, prior to scaling the selected arch form, the method includes selecting a reference tooth. Scaling the selected arch form may then be based on the selected reference tooth.

In one embodiment, scaling the selected ideal arch form includes measuring a location of the reference tooth in the model and calculating an aspect ratio of the reference tooth based on the location measured. In one embodiment, the method further includes identifying coordinates on the ideal arch form based on the calculated aspect ratio so that scaling includes resizing the ideal arch form based on the coordinates identified.

In one embodiment, measuring includes measuring a width and a height of the reference tooth location in the model of the set of teeth.

In one embodiment, the method further comprises repositioning the reference tooth in the model prior to scaling the selected arch form.

In one embodiment, repositioning includes aligning a buccal ridge of the other tooth with the scaled arch form. This may include aligning the buccal ridge of the other tooth to be tangent to the scaled arch form.

In one embodiment, the ideal arch form is configured to be computationally evaluated at any given point along its length. This may include a situation in which the ideal arch form is represented by a closed-form mathematical formulation.

In one embodiment, the ideal arch form is defined by unique aspect ratios along the arch form.

In one embodiment, the method further includes storing a plurality of arch forms in a raw arch form database. This may include using the algorithm to select from the raw arch form database based on one or more patient characteristics.

In accordance with the principles of the present invention, a system for digital orthodontic setup from a digital model of a patient's teeth includes a processor and a memory being coupled to the processor. The memory includes instructions that, when executed by the processor, cause the system to: (i) select an arch form for the patient's teeth from a database of a plurality of arch forms; (ii) scale the selected arch form to fit at least one tooth in the digital model; (iii) generate a prescribed setup for the patient's teeth based on the scaled arch form; and (iv) prepare information in accordance with the prescribed setup to have an orthodontic appliance manufactured for treatment of the patient.

In one embodiment, the scale of the selected arch form is based on at least one reference tooth in the digital model.

In one embodiment, the memory includes instructions that, when executed by the processor, cause the system to reposition the one reference tooth in the digital model and the selected arch form is based on the repositioned reference tooth.

In one embodiment, the memory includes instructions that, when executed by the processor, cause the system to reposition at least one other tooth in the digital model so as to have at least one of a buccal ridge or a marginal ridge of the other tooth to be tangent to the scaled arch form.

In one embodiment, the system further includes a raw arch form database including a plurality of arch forms and the selected arch form is one of the plurality of arch forms. Each of the plurality of arch forms may be unique.

In accordance with the principles of the present invention, a computer program product useable to treat teeth of a patient includes a non-transitory computer-readable storage medium and instructions stored on the non-transitory computer-readable storage medium that, when executed by a processor, cause the processor to: (i) scale an arch form selected from a database of a plurality of arch forms to fit a digital model of the patient's teeth; (ii) generate a prescribed setup for the patient's teeth based on the scaled arch form; and (iii) prepare information in accordance with the prescribed setup to have an orthodontic appliance manufactured for treatment of the patient.

BRIEF DESCRIPTION OF THE DRAWINGS

The accompanying drawings, that are incorporated in and constitute a part of this specification, illustrate various embodiments of the invention and, together with the detailed description of the embodiments given below, serve to explain the embodiments of the invention.

DETAILED DESCRIPTION

Figure 1:
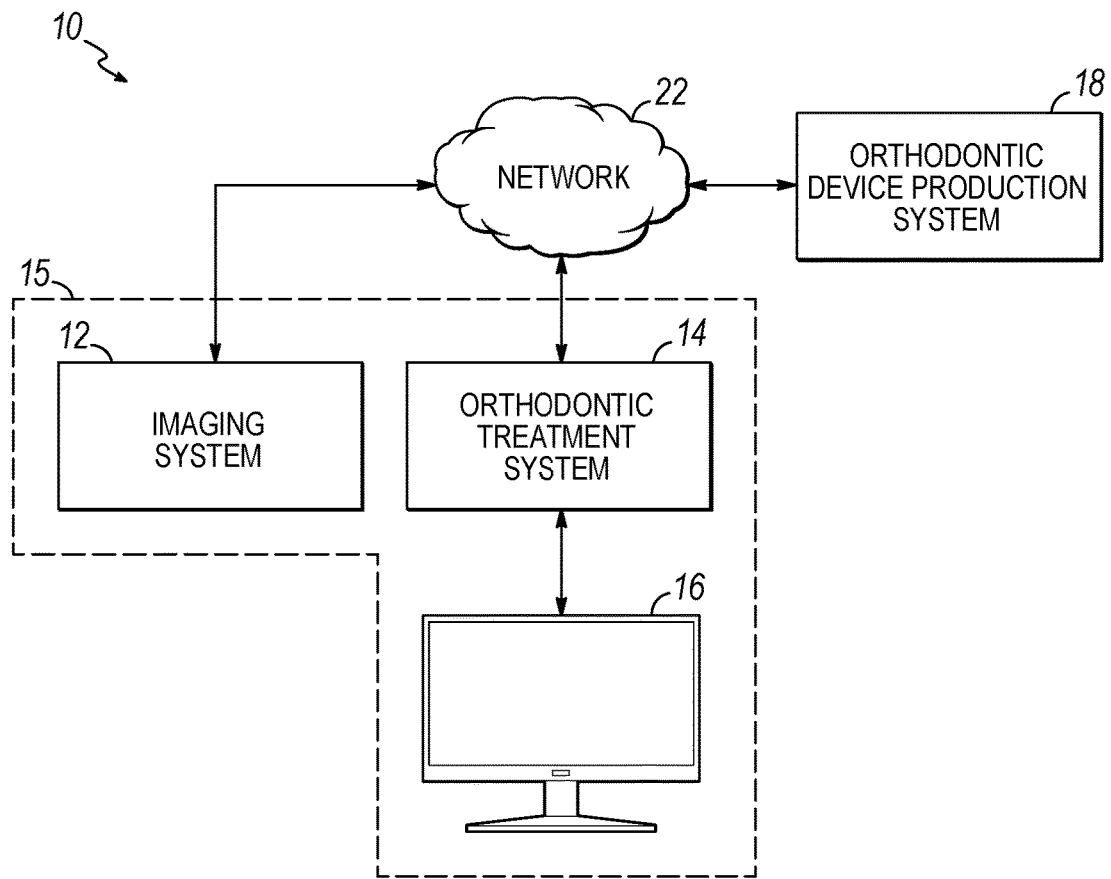
FIG. 1 is a diagrammatic view of an exemplary operating environment including an orthodontic treatment system and a display system in communication with an imaging system and an orthodontic device production system via a network.

Embodiments of the invention are directed to methods, systems, and computer program products for digital orthodontic setup using a prescribed ideal arch form. Embodiments of the invention may be implemented by or include an imaging system configured to acquire digital images of the patient's teeth. Embodiments of the invention may be implemented by or include an orthodontic device production system, whereby a prescribed setup may be used to manufacture an orthodontic device. Embodiments of the invention may be implemented by or include an orthodontic treatment system comprising one or more networked computers or servers. The orthodontic treatment system may include a preprocessing module coupled with a raw image database for facilitating the acquisition and initial setup of the digital images of the patient's teeth. Reference teeth may be manipulated through an interface of a display system connected to the orthodontic treatment system, whereby the interface and display system accesses and displays the digital images through communication with a memory and the preprocessing module. Reference teeth may be moved and set in accordance with the dental practitioner's preferences and clinical experience or automatically via an algorithm developed from historical information of orthodontic treatment.

After at least one reference tooth is set by the dental practitioner, an arch form is selected for use in the dental setup. The arch form may be selected by the dental practitioner from a raw arch form database through an arch form selection module accessible through the interface of the display system. In one embodiment, the dental practitioner may reposition at least one reference tooth, but selection of the arch form to fit the reference teeth is based on an algorithm and thus occurs automatically without the practitioner's further input. Advantageously, eliminating further input of the clinician may remove human error from the treatment process and so produce more uniform, more consistent treatment.

The arch forms in the raw arch form database may be unit-less arch forms, having no specific size or scale with respect to the digital model of the patient's teeth. As such, the unit-less arch forms may be scaled to fit any size patient, from a youth to a full grown adult set of teeth. Inasmuch as the reference teeth are set and adjusted by the dental practitioner, once the arch form is selected, an arch form scaling module scales the selected arch form to fit the reference teeth of the digital model. Thereafter, the remaining teeth are adjusted, either manually or automatically, to fit the scaled arch form. An automatic alignment algorithm may be configured to align the buccal ridges of the teeth to be tangent to the scaled arch form, align the marginal ridges of the teeth to be tangent to the scaled arch form, maintain each tooth a proper interproximal distance apart from one another, or a combination thereof for each tooth.

In addition to being unit-less, the arch forms in the raw arch form database may be ideal arch forms. Ideal arch forms may be computationally evaluated at any point along the arch. For example, each arch form may be represented by a closed form mathematical formulation, a look-up table, or any other relationship by which any point on the arch form may be specifically located and identified, such as via coordinates (e.g., x and y coordinates). Further, ideal arch forms include a unique aspect ratio at any point along the arch, whereby the ratio between a width and a depth of any point along the arch is unique. Satisfaction of the uniqueness of the points along the arch and aspect ratio for an ideal arch form allows the arch form to be scaled to fit any individual patient.

Referring now to FIG. 1, an operating environment 10 in accordance with an embodiment of the invention may include an imaging system 12, an orthodontic treatment system 14 in communication with a display system 16, and an orthodontic device production system 18. Imaging system 12, orthodontic treatment system 14, and display 16 may be located in an office 15 of the dental practitioner. Each of imaging system 12, orthodontic treatment system 14, and orthodontic device production system 18 may communicate through a network 22. Network 22 may include one or more private or public networks (e.g., the Internet) that enable the exchange of data.

Figure 2:
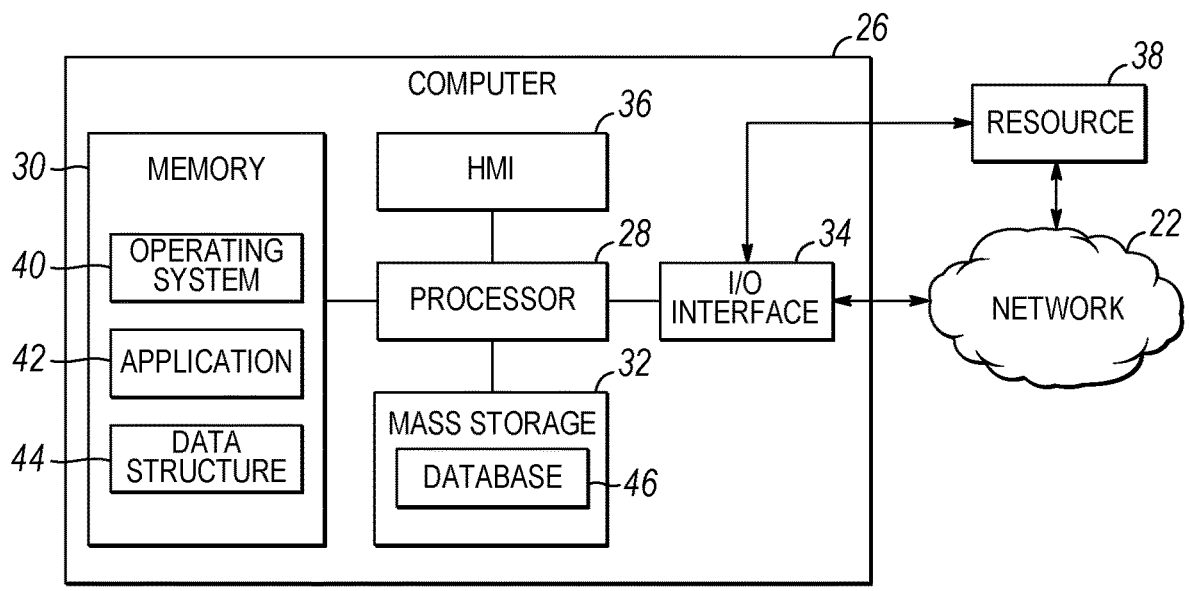
FIG. 2 is a diagrammatic view of an exemplary computer system of FIG. 1.

Referring now to FIGS. 1 and 2, imaging system 12, orthodontic treatment system 14, and orthodontic device production system 18 of operating environment 10 may be implemented on one or more computer devices or systems, such as exemplary computer system 26. The computer system 26 may include a processor 28, a memory 30, a mass storage memory device 32, an input/output (I/O) interface 34, and a Human Machine Interface (HMI) 36. The computer system 26 may also be operatively coupled to one or more external resources 38 via the network 22 or interface 34. External resources may include, but are not limited to, servers, databases, mass storage devices, peripheral devices, cloud-based network services, or any other suitable computer resource that may used by the computer system 26.

The processor 28 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 30. Memory 30 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or any other device capable of storing information. The mass storage memory device 32 may include data storage devices such as a hard drive, optical drive, tape drive, non-volatile solid state device, or any other device capable of storing information.

Processor 28 may operate under the control of an operating system 40 that resides in memory 30. The operating system 40 may manage computer resources so that computer program code embodied as one or more computer software applications, such as an application 42 residing in memory 30, may have instructions executed by the processor 28. In an alternative embodiment, the processor 28 may execute the application 42 directly, in which case the operating system 40 may be omitted. One or more data structures 44 may also reside in memory 30, and may be used by the processor 28, operating system 40, or application 42 to store or manipulate data.

The interface 34 may provide a machine interface that operatively couples the processor 28 to other devices and systems, such as the network 22 or external resource 38. The application 42 may thereby work cooperatively with the network 22 or external resource 38 by communicating via the interface 34 to provide the various features, functions, applications, processes, or modules comprising embodiments of the invention. The application 42 may also have program code that is executed by one or more external resources 38, or otherwise rely on functions or signals provided by other system or network components external to the computer system 26. Indeed, given the nearly endless hardware and software configurations possible, persons having ordinary skill in the art will understand that embodiments of the invention may include applications that are located externally to the computer system 26, distributed among multiple computers or other external resources 38, or provided by computing resources (hardware and software) that are provided as a service over the network 22, such as a cloud computing service.

The HMI 36 may be operatively coupled to the processor 28 of computer system 26 in a known manner to allow a user to interact directly with the computer system 26. The HMI 36 may include video or alphanumeric displays, a touch screen, a speaker, and any other suitable audio and visual indicators capable of providing data to the user. The HMI 36 may also include input devices and controls such as an alphanumeric keyboard, a pointing device, keypads, push-buttons, control knobs, microphones, etc., capable of accepting commands or input from the user and transmitting the entered input to the processor 28.

A database 46 may reside on the mass storage memory device 32, and may be used to collect and organize data used by the various systems and modules described herein. The database 46 may include data and supporting data structures that store and organize the data. In particular, the database 46 may be arranged with any database organization or structure including, but not limited to, a relational database, a hierarchical database, a look-up table, a network database, or combinations thereof. A database management system in the form of a computer software application executing instructions on the processor 28 may be used to access the information or data stored in records of the database 46 in response to a query, where a query may be dynamically determined and executed by the operating system 40, other applications 42, or one or more modules.

In an embodiment of the invention, the database 46 may comprise a raw image database 48 (FIG. 3) configured to store and retrieve image data of a patient's teeth and surrounding tissue acquired from imaging system 12. Database 46 may also comprise a raw arch form database 50 (FIG. 3) configured to store and retrieve arch form data collected or constructed for use in the present invention. Database 46 may also comprise a treatment database 52 (FIG. 3) configured to store and retrieve data regarding the treatment plan prescribed by the dental practitioner and any data associated therewith.

Figure 3:
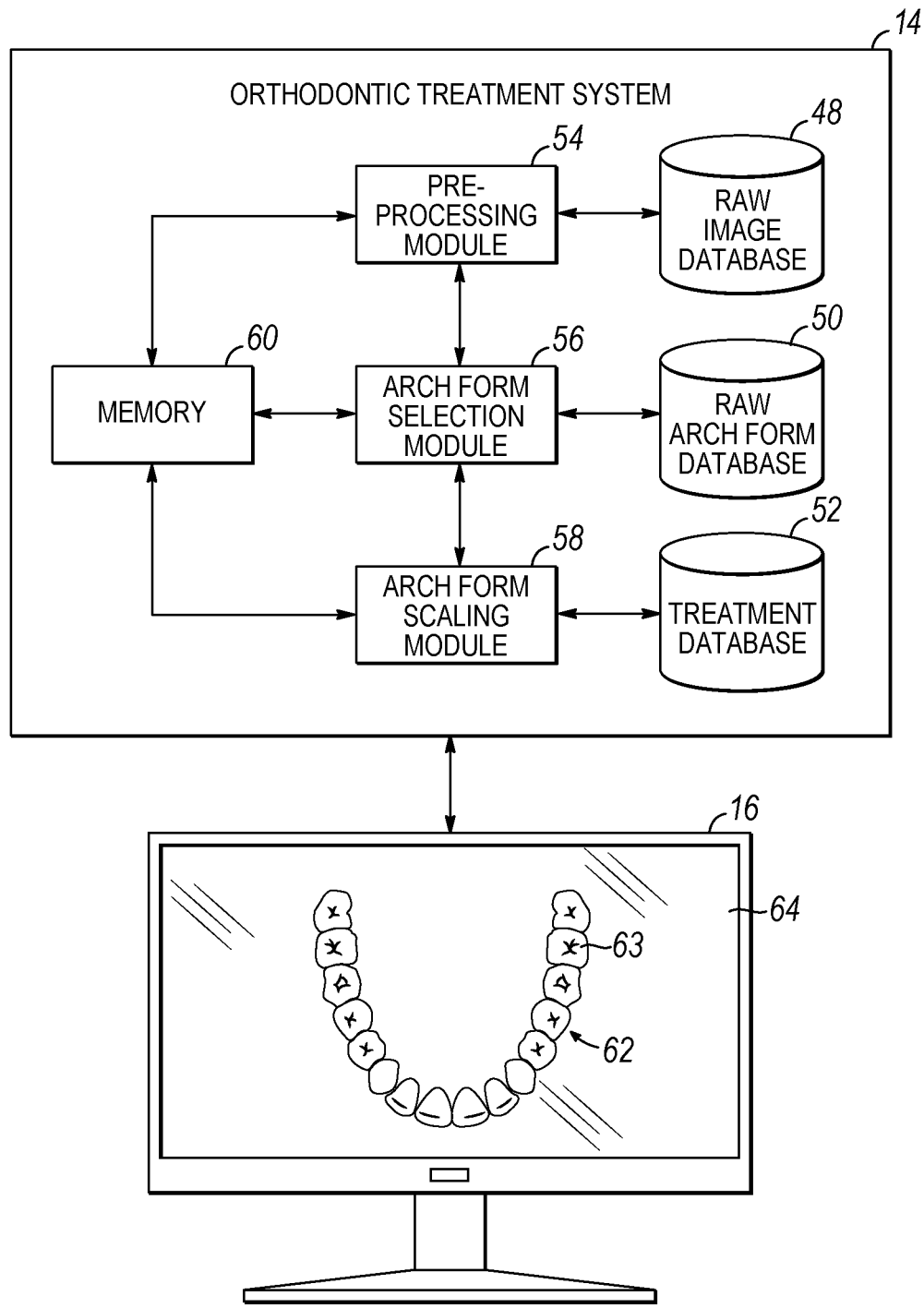
FIG. 3 is a diagrammatic view of the orthodontic treatment system and display system of FIG. 1.

Referring now to FIG. 3, an orthodontic treatment system 14 may include a preprocessing module 54, an arch form selection module 56, an arch form scaling module 58, and a memory 60. In one embodiment, memory 60 includes memory 30 of computer system 26 shown in FIG. 3. Orthodontic treatment system 14 may be configured such that each module and database communicates therebetween. Alternatively, orthodontic treatment system 14 may be configured such that each module may be configured to communicate primarily with a corresponding database and memory 60, whereby each module accesses memory 60 to perform the methods or tasks of the present invention. In an exemplary embodiment of the invention, preprocessing module 54 is configured to communicate with raw image database 48, arch form selection module 56, and memory 60; arch form selection module 56 is configured to communicate with raw arch form database 50, preprocessing module 54, memory 60, and arch form scaling module 58; and arch form scaling module 58 is configured to communicate with treatment database 52, arch form selection module 56, and memory 60.

In an embodiment of the invention, raw images of the patient's teeth are scanned or acquired through imaging system 12 and digitally stored in raw image database 48. Preprocessing module 54 is configured to retrieve the raw images of the patient's teeth from raw image database 48 and present these images as a plurality of virtual teeth 62 through display 16 to the dental practitioner. With these images, a digital model may be created and with reference to FIG. 3, the dental practitioner may initially define an occlusal plane (not labeled) in the model. By way of example only and not limitation, the occlusal plane may be defined by a specific midpoint of the two mandibular central incisors and the mesiobuccal cusp tip points of the two mandibular first molars. Because the patient's untreated teeth may exhibit some misalignment, the manual manipulation may comprise selecting and moving one or more reference teeth in the plurality of virtual teeth 62. For example, the dental practitioner may select the two mandibular first molars and may thereafter adjust the selected molars to a certain position and angle within the model of the patient's teeth. Further in that regard, the two first molars may be adjusted in accordance with the "Curve of Wilson," a setup guideline adopted by many orthodontists.

Figure 6:
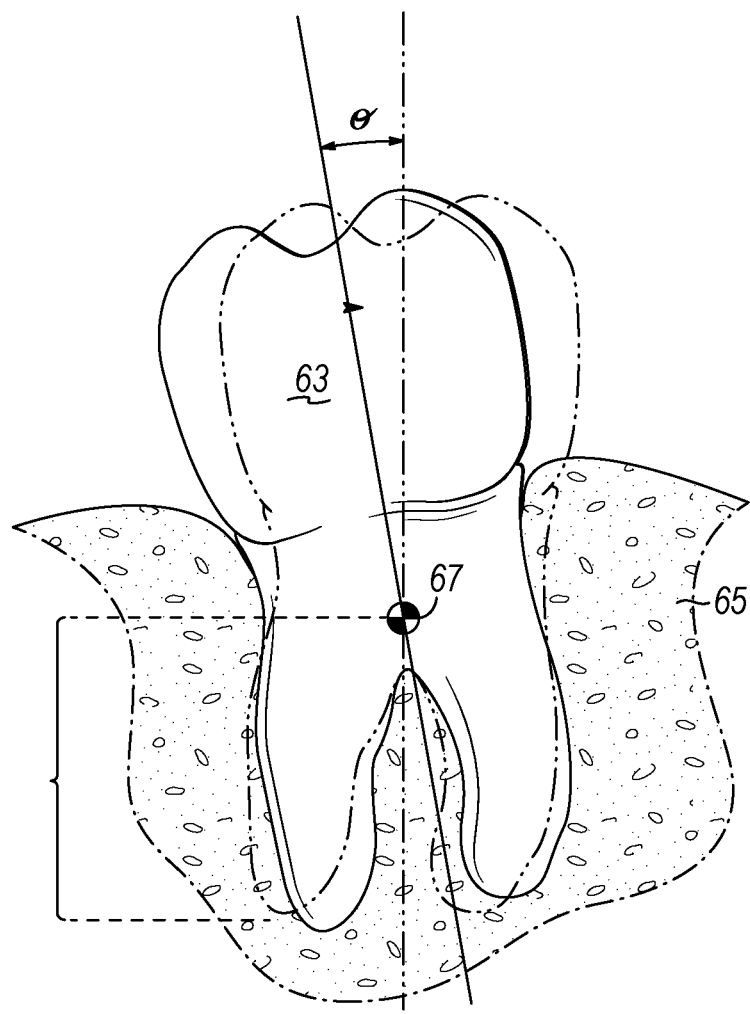
FIG. 6 is a side elevational view of an exemplary tooth within a patient's gingiva.

As shown in FIG. 6, a reference tooth 63 may be adjusted within a root structure 65 about an axis 67 by a particular θ. In an exemplary embodiment of the invention, a particular θ is equal to approximately ten degrees in the lingual direction (this may be referred to as "upright"). Alternatively, reference tooth 63 may be oriented in three-dimensional space to conform to the natural occlusal plane inclination of the patient or may be adjusted by setting the two mandibular first molars to the same depth within the root structure 65. The upper arch, i.e., the maxillary arch, may be similarly manipulated to place teeth on that arch into good occlusion with the mandibular teeth. As is described below, each reference tooth 63 may define a width and a height of a particular location along the arch.

In an embodiment of the invention, after a dental practitioner optionally adjusts selected reference teeth 63 in accordance with the dental practitioner's preferences, the updated plurality of virtual teeth 62 are stored in memory 60 for further use in orthodontic treatment system 14. Other embodiments of the invention may store the updated teeth 62 in any other location or mechanism for saving the dental practitioner's adjustments with respect to the original raw images acquired from the patient's mouth. Thereafter, the dental practitioner selects an arch form from raw arch form database 50 by way of interface 34 in conjunction with display 16 and arch form selection module 56. In one embodiment, the selection module 56 may automatically determine the arch form for the patient. This determination may be based on information about the patient including characteristics, such as the age, gender, and race of the patient. In either case, arch form selection module 56 retrieves an arch form from raw arch form database 50 and thereafter stores the selected arch form in memory 60 for further use in orthodontic treatment system 14. In an embodiment of the invention, each arch form stored in raw arch form database 50 is unit-less and is not restricted to a particular size or scale with respect to the plurality of virtual teeth 62.

In one embodiment of the invention, each arch form stored in raw arch form database 50 is an ideal arch form and can be computationally evaluated at any given point along the arch form. Computationally evaluating the arch form may include having a closed form mathematical formulation, an existing look-up table, or any other mechanism for generating or deriving coordinates of one or more of a plurality of points along the ideal arch form. Further, each arch form stored in raw arch form database 50 may include a unique aspect ratio at any point, whereby the ratio between a measured width and a measured height of a point along the arch form is unique. An exemplary ideal arch form 68 of the present invention embodying unique aspect ratios is illustrated in each of FIGS. 4A and 4B.

Figure 4A:
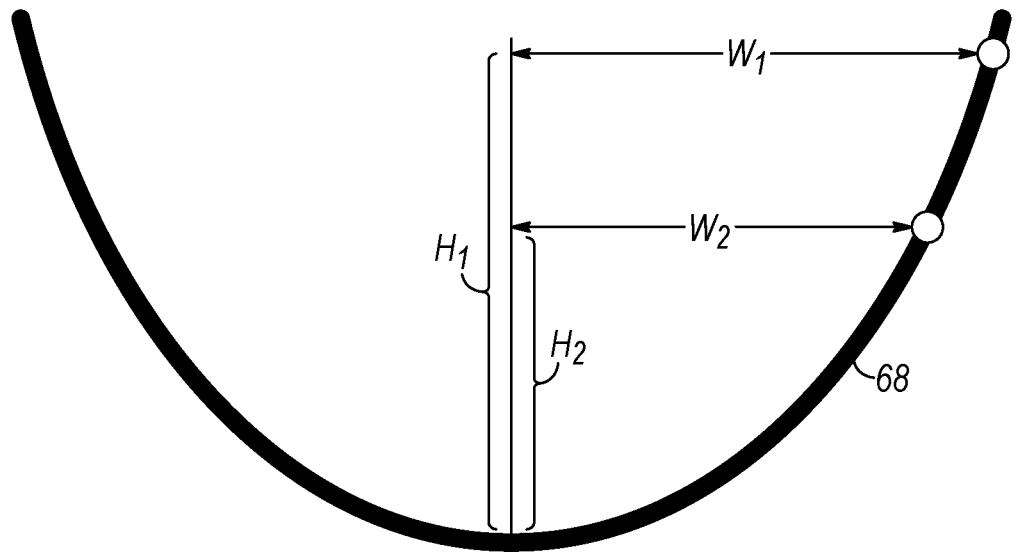
FIGS. 4A and 4B are diagrammatic views of two different exemplary arch forms according to embodiments of the invention.
Figure 4B:
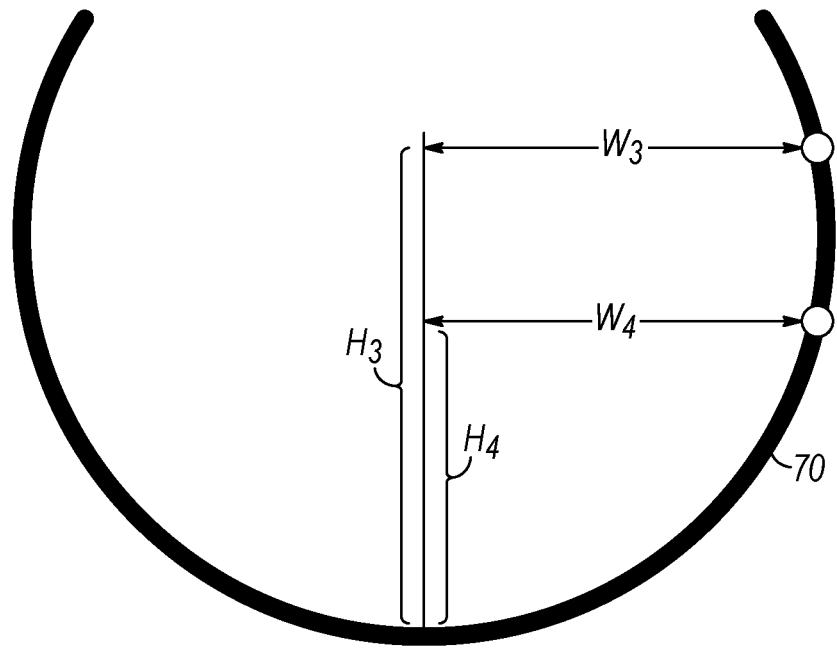
Figure 5A:
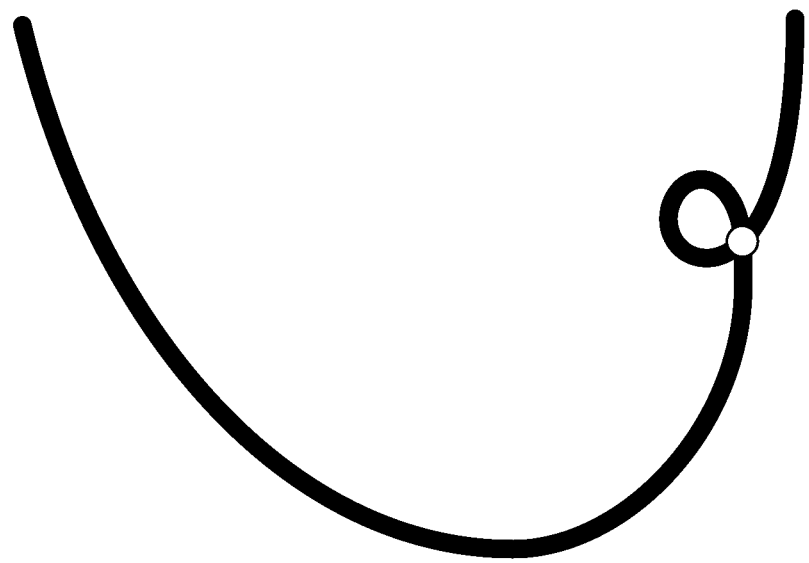
FIGS. 5A and 5B are diagrammatic views of two different exemplary arch forms.
Figure 5B:
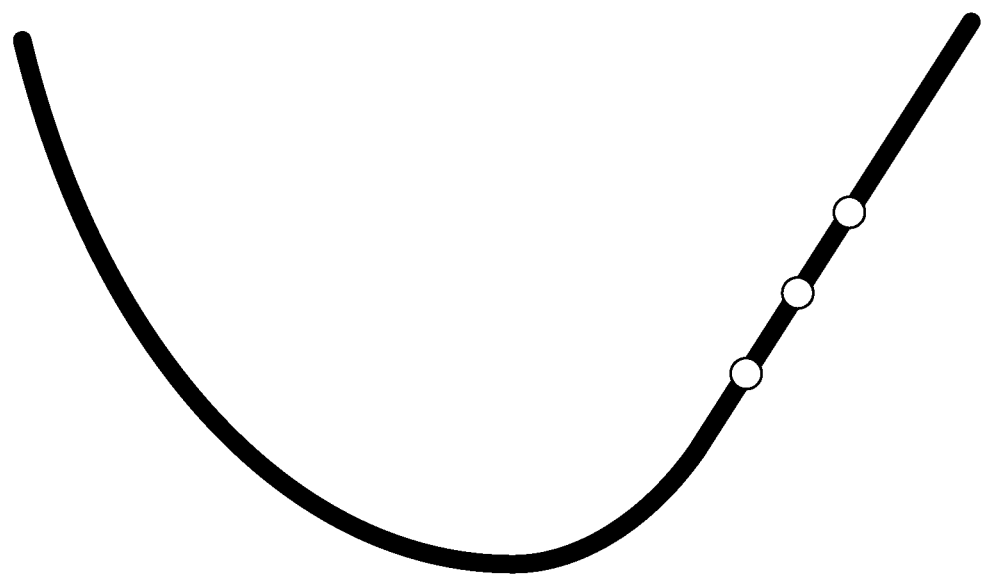

As shown in FIG. 4A, the arch form 68 has unique aspect ratios everywhere. For example, the value of a ratio of a particular width $W_1$ to a particular height $H_1$ is different than all other ratios including, for example, the value of a ratio of a particular width $W_2$ to a particular height $H_2$. Another arch form 70 embodying unique aspect ratios is illustrated in FIG. 4B, whereby the value of the ratio of a particular width $W_3$ to a particular height $H_3$ is different than the value of the ratio of a particular width $W_4$ to a particular height $H_4$. Even though $W_3$ may be about the same as $W_4$, $H_3$ is substantially different from $H_4$. As such, in an embodiment of the invention, arch form 70 is also an acceptable arch form for use by orthodontic treatment system 14. While FIGS. 4A and 4B illustrate arch forms according to embodiments of the invention, FIGS. 5A and 5B illustrate embodiments which may not be acceptable arch forms. Further in that regard, according to FIG. 5A, the arch form may not self intersect and according to FIG. 5B, the arch may not follow a straight line on any portion of the arch.

Arch forms 68, 70 may be evaluated and have unique aspect ratios at any point. These arch forms may be scaled to each individual patient. For example, adults and teenagers could both be treated to the same ideal arch form, even though their jaw bones have very different sizes and anatomical proportions. Reference teeth may provide for proper scaling of a unit-less arch form to a set of teeth. For example, one reference tooth at the center of the arch and a reference tooth along each branch of the arch may cooperate or be used singly to scale an individual arch form to a particular patient's teeth.

Figure 7A:
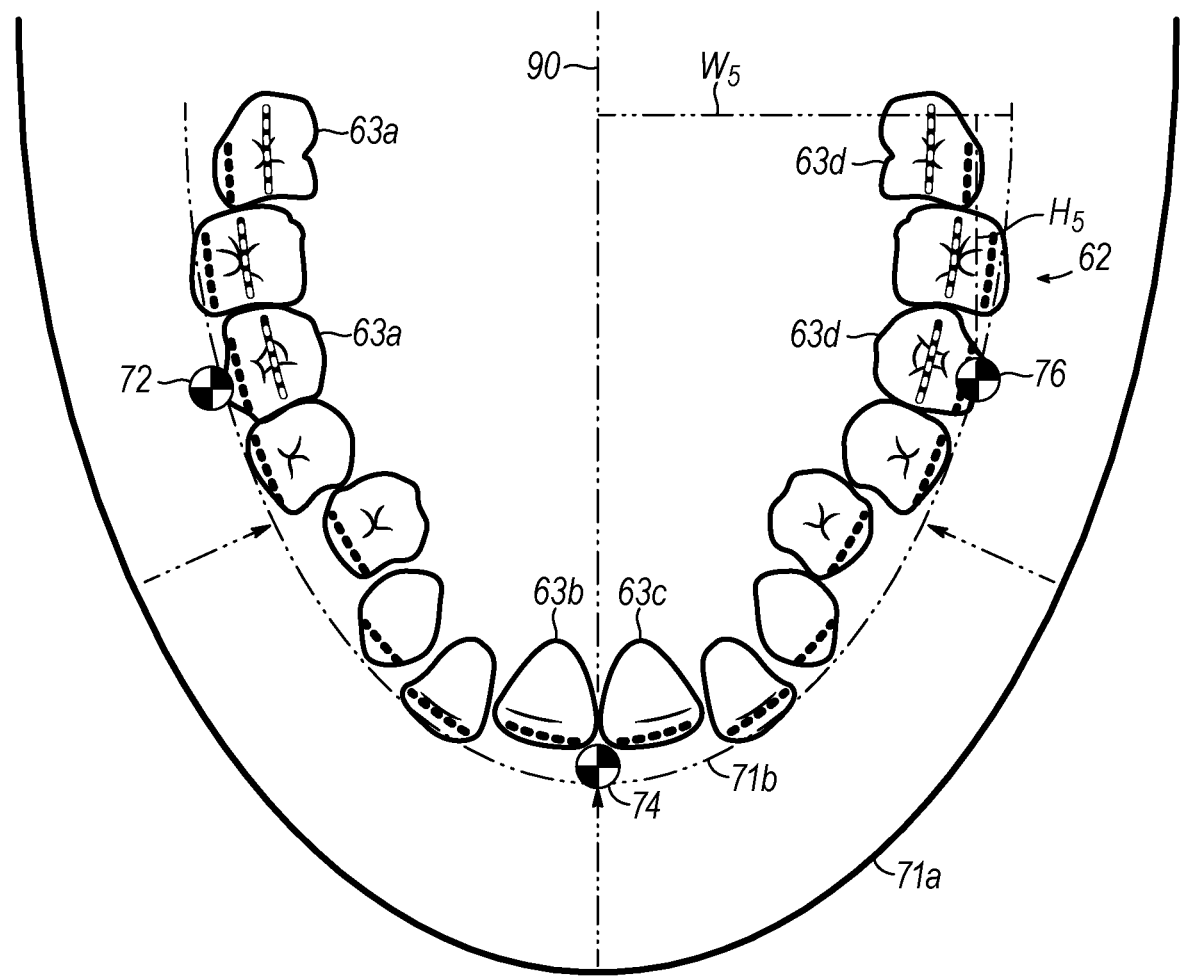
FIG. 7A is a top plan view of an exemplary set of teeth and an arch form.

As shown in FIG. 7A, to scale a selected arch form 71a to fit the set of teeth 62, reference points may be used. Reference points may be determined by reference teeth that are selected, and if necessary virtually moved, as described above. For example, a reference tooth 63a may be adjusted by the dental practitioner to serve as a branch reference point 72, reference teeth 63b and 63c may be adjusted by the dental practitioner to serve as a central reference point 74 (which may determine the location of a mid line 90), and reference tooth 63d may be adjusted by the dental practitioner to serve as a branch reference point 76.

After the reference teeth are repositioned, if necessary, and the reference points are derived, the arch form scaling module 58 calculates a scaling factor. The scaling factor may be determined by measuring a particular height, $H_5$, and a width, $W_5$, at the reference point 76. Height $H_5$ and width $W_5$ may represent actual measurements of the reference point 76 for the arch from an arbitrarily selected origin. Each of the origin and reference point may lie in a plane. In this exemplary embodiment, the origin lies on mid line 90. Width $W_5$ may be measured perpendicularly from the mid line 90 to a line parallel to the mid line 90 that passes through reference point 76. Height $H_5$ is measured perpendicularly from the line that defines $W_5$ to reference point 76. These measurements, which may be thought of as a location of the reference point 76 relative to the origin, are then utilized by the arch form scaling module 58 to calculate an aspect ratio. For example, a specific aspect ratio, $A/R_5$, at the reference point 76 is then calculated from the ratio of height $H_5$ and width $W_5$. The arch form 71a has a matching aspect ratio to which is assigned coordinates within the same coordinate system defined by the selected origin. With the calculated aspect ratio $A/R_5$, the matching aspect ratio of the arch form 71a, the coordinates at that location on the ideal arch form, and the location of the reference point 76 all being known, a scaling factor may be calculated. With the scaling factor, the arch form 71a is scaled to the arch form 71b.

Figure 7B:
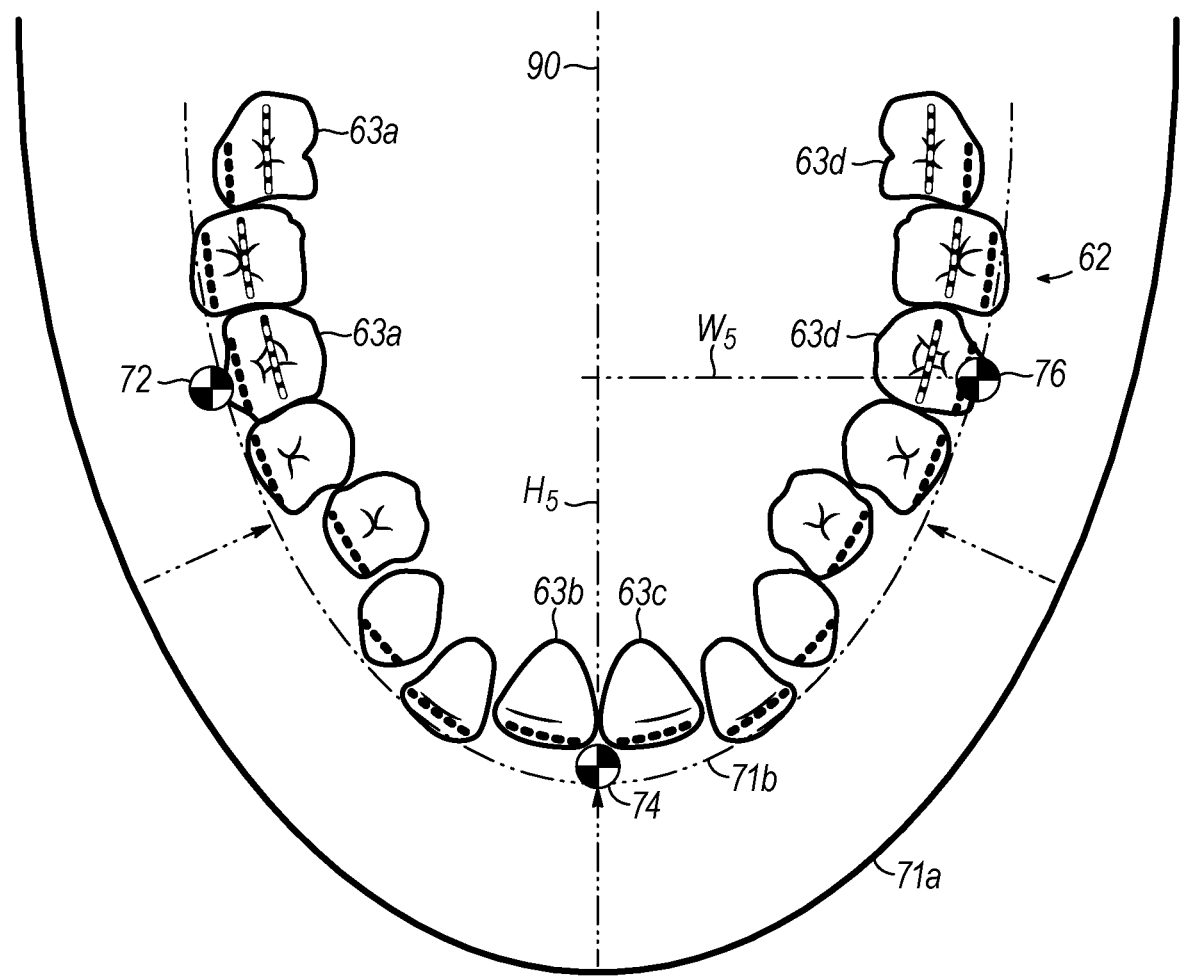
FIG. 7B is a top plan view of another exemplary set of teeth and an arch form.

It will be appreciated that other reference points (i.e., other locations on the arch) may be utilized to calculate the scaling factor or to cross-check the initial calculated scaling factor based on the reference point 76. For example, arch form scaling module 58 may compute an aspect ratio based upon branch reference point 72 and based on central reference point 74. These aspect ratios may be used to independently assess the scaling factor based on reference point 76 or be used to assess the symmetry of the patient's arch. As yet another example, and with reference to FIG. 7B, an alternative origin may be utilized in the measurement of reference point 76. As shown, reference point 74 may be the location of the origin from which $H_5$ and $W_5$ are measured to determine the location of reference point 76. Once that reference point is located, the arch form scaling module 58 may calculate the aspect ratio and ultimately the scaling factor as described above. In this way, the arch form 71a may be scaled to the arch form 71b based on another origin. In one embodiment, the origin selected for locating the reference points 72, 74, 76 corresponds to the origin for coordinates of the ideal arch form 71a.

As an optional verification step, arch form scaling module 58 may thereafter use the computed aspect ratios with respect to the arch form 71b to determine if branch reference point 76 aligns with the proposed scaled arch form 71b. If the scaled arch form 71b aligns to branch reference point 76 with the appropriate alignment, arch form scaling module 58 may consider the aspect ratio value proper and correct. If the scaled arch form 71b does not properly align with branch reference point 76, arch form scaling module 58 may alert the dental practitioner or take further steps to rectify the improperly scaled arch form 71b. Alternatively, the dental practitioner may optionally decide to not enforce strict bi-lateral symmetry between the left and right branches of arch form 71b and, as such, arch form scaling module 58 may determine two different scaling factors for arch form 71b (not shown) by deriving one scaling factor for each branch reference point 72 and 76 and then scaling the arch form 71a with those scale factors.

Alternatively, the arch form scaling module 58 may calculate a scaling factor for an arch form that may be defined by multiple arcs with or without straight segments. In an exemplary embodiment of the invention and with reference to FIG. 10, an ideal arch form 92 may be defined by three unit-less arcs R1, R2, and R3 and, optionally, two straight segments S1 and S2. As shown, the arch form 92 may be symmetrical about a line CMF, described below. However, it will be appreciated that symmetry is not always necessary so that embodiments of the invention may include nonsymmetrical arch forms. As with arch form 71a, the arch form 92 defines unique aspect ratios along its entire length. Each aspect ratio of arch form 92 is assigned unit-less coordinates. Thus, the coordinates of any point along the length of the arch form 92 may be determined by an initial determination of an aspect ratio. In turn, the aspect ratio may be initially calculated from measurement of one or more reference tooth locations. The initial measurement of the reference tooth may then determine the units (i.e., the scale) and coordinates of the arch form 92 at a particular aspect ratio that is common to both the arch form 92 and one of the reference teeth 63a, 63b, 63c, 63d.

Figure 10:
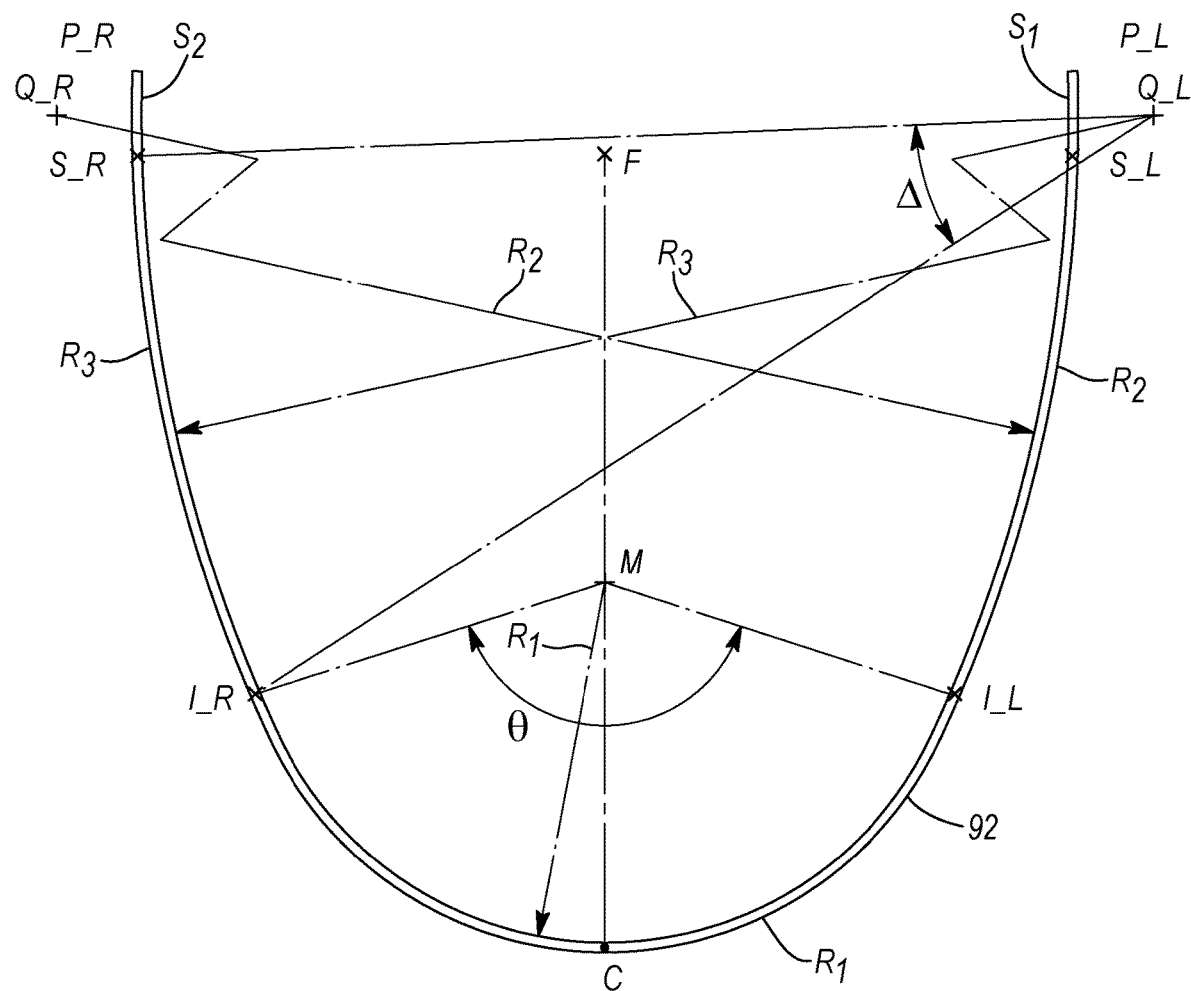
FIG. 10 is a top plan view of an exemplary arch form according to one embodiment of the invention.

In an exemplary embodiment shown in FIG. 10, the radius of R1 is 1.060 and the radius of R2 is 4.250. The radius of R3 may be equal to the radius of R2, though it is not necessary that the radius of R2 and the radius of R3 be equal to one another if no bilateral symmetry is maintained. R1 may span an angle, $\Theta$, of about 65.2° between intersections of R1 with R2 at one end and R3 at an opposing end. R2 and R3 may each span an angle, A, of about 24.8° to the intersection with R1 at one end and S1 and S2, respectively, at the other end. Each of the arcs R1, R2, and R3 and segments S1 and S2 of the ideal arch form 92 may be parameterized. In this way, a parameterized point on the arch form 92 may be linked by an aspect ratio to a physical measurement of one of the reference tooth locations.

For example, points along the arch form 92 may be parameterized by assigning each of a plurality of unique aspect ratios along the arch form 92 to a unit-less coordinate. By measuring and calculating a specific aspect ratio of a reference tooth, the unit-less coordinate for that aspect ratio is determined from the parameterization. The units associated with the coordinate are determined by the units of the measurement of the reference tooth. The arch form 92 may then be scaled to the reference tooth with this information.

By way of example, and with continued reference to FIG. 10, the coordinates defining R1 may be parameterized on the ideal arch form 92 according to a radius of R1 represented by "C_CM·r" in which r is a scaling factor. If, for example, the radius of R1 is 1.060 and C_CM is arbitrarily assigned to be 1.0 then r=1.060. The center, M, of R1 may be determined by locating the midpoint of the ideal arch form 92 at C and then measuring a distance of C_CM (in the exemplary form C_CM=1) from C.

The intersection of R2 with S1 and the intersection of R3 with S1 may be determined by measuring a distance of "C_MF·r" in which C_MF=1.262264 from M along the line established by M and C to a point F and then moving perpendicularly to line CMF by a distance equal to "C_FS·r" in which C_FS=1.277358 toward S1 to define S_L. An intersection between R2 and S1 occurs at S_L. Similarly, in a case in which bilateral symmetry is maintained, moving perpendicularly to line CMF by a distance equal to C_FS·r toward S2 establishes an intersection between R3 and S2 at S_R.

From F, each of the centers Q_R and Q_L of R2 and R3, respectively, may be established by measuring a distance "C_FQ·r" in which C_FQ=2.732075 perpendicularly to line CMF at F. The coordinates along R2 and R3 may also be parameterized on the ideal arch form 92 according to "C_RR·r," which may represent the radius R2 and/or R3 at centers Q_L and Q_R, respectively. For example, if the radius of R2 and the radius of R3 are each 4.250 and r=1.060 then C_RR=4.250/1.060, so that C_RR=4.00943.

One or both of the segments S1 and S2 may linearly extend from S_L and S_R, respectively, by a distance "C_SP·r" in which C_SP=0.115094 to end points P_R and P_L, respectively. As with R1, R2, and R3, points along each of S1 and S2 may be parameterized. The intersections between R1 and R2 (i.e., I_L) and between R1 and R3 (i.e., I_R) may be determined by a relationship between Θ and Δ according to the equation: Θ/Θ+C_RR·A+C_SP where Θ is in radians. It will be appreciated that measurements to establish the shape of the arch form 92 may be made in any units as long as each measurement is made in the same unit. That is, the measurements are uniform throughout the arch form 92. This produces an arch form shape that is essentially unit-less and is scalable to any patient. Furthermore, it will be appreciated that the numerical values of at least any single one of C_CM, C_MF, C_FQ, C_RR, and C_SP may vary from the values given. The value of each may be determined based on clinical experience and/or historical treatment data that may take into account the ages, genders, and ethnicities of a large pool of patients.

In view of the above relationships, each of a plurality of aspect ratios links a parameterized point on the ideal arch form 92 defined by R1, R2, R3, S1 and S2 to a measurable location of teeth in the patient's mouth. Measuring the location of a reference tooth may also determine the scaling factor r. Once r is known, the arch form 92 may then be scaled because in the exemplary embodiment each of R1, R2, R3, S1, and S2 is proportional to the value of r. According to embodiments of the invention, a clinician may first determine an aspect ratio of a reference tooth. Because that unique aspect ratio is linked to a particular parameterized point on the arch form 92, the units of the parameterized point may be determined. Once known, the remainder of the coordinates along the arch form 92 and scale of the arch form 92 can then be determined so that the scaled arch form may fit one or more of the reference teeth.

Figure 8:
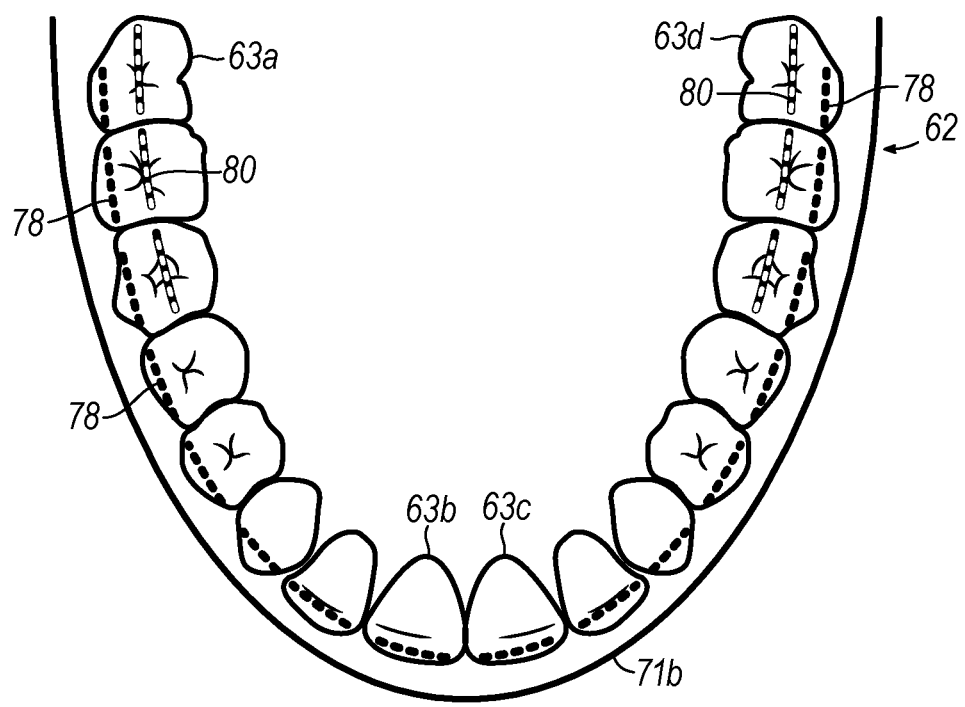
FIG. 8 is a top plan view of an exemplary set of teeth aligned with an arch form according to one embodiment of the invention.

Referring now to FIGS. 7 and 8, after the aspect ratio value is determined and arch form 71b or arch form 92 is adjusted to fit the patient, the majority of the set of teeth 62 are not properly aligned to the adjusted arch form 71b, 92. Once the arch form 71b, 92 is adapted to fit the patient and the set of teeth 62, setup of all of the remaining teeth can be performed by aligning reference landmarks for each tooth to the arch form while keeping proper interproximal distances between them. For example, many teeth 62 may include a buccal ridge 78 or a marginal ridge 80 as a reference landmark. To align the remaining teeth 62 with the arch form 71b, 92, each buccal ridge 78 or marginal ridge 80 may be aligned to be tangent to arch form 71b, 92. Aligning of the teeth to the scaled arch form 71b, 92 may be done automatically by arch form scaling module 58 or another module in orthodontic treatment system 14. Alternatively, the dental practitioner may manually, through interface 64, manipulate the remaining teeth 62 into proper position with respect to scaled arch form 71b, 92. Once each tooth in the set of teeth 62 is aligned with the scaled arch form 71b, 92, the final alignment may be approved and prescribed by the dental practitioner, and referred to hereinafter as the prescribed setup.

From an orthodontic perspective, the prescribed setup using an embodiment of the invention is minimal and most natural. The individualized arch form is derived by scaling to fit selected ones or each of the reference teeth 63a, 63b, 63c, 63d, rather than the reference teeth moving to reach an arbitrarily defined shape. Any preliminary adjustments done to the reference teeth are at the discretion of the dental practitioner and typically medically necessary from an orthodontic standpoint, and therefore unavoidable. Further, the remainder of the teeth are aligned to the scaled arch form while maintaining alignment of landmarks such as buccal ridges and marginal ridges, which are naturally formed anatomical features. The ideal arch form may be automatically prescribed based upon statistical or radiographic analysis of previously prescribed arch forms. For example, treatment outcomes may be tracked from image scan data from patients having common characteristics, such as ethnicity or dietary pattern. From the tracked treatment outcomes, conclusions may be drawn to determine that people in a particular group largely share the same ideal arch form.

As shown in FIG. 3, after completing the prescribed setup, a database entry encapsulating the prescribed setup may be stored in treatment database 52 for further use by orthodontic treatment system 14 or for further use in operating environment 10. For example, orthodontic treatment system 14 may transmit data representing the prescribed setup to orthodontic device production system 18. Orthodontic device production system 18 may thereafter use the prescribed setup to manufacture orthodontic braces or aligners in accordance with the prescribed setup for use by the patient in accordance with the treatment prescribed by the clinician.

Figure 9:
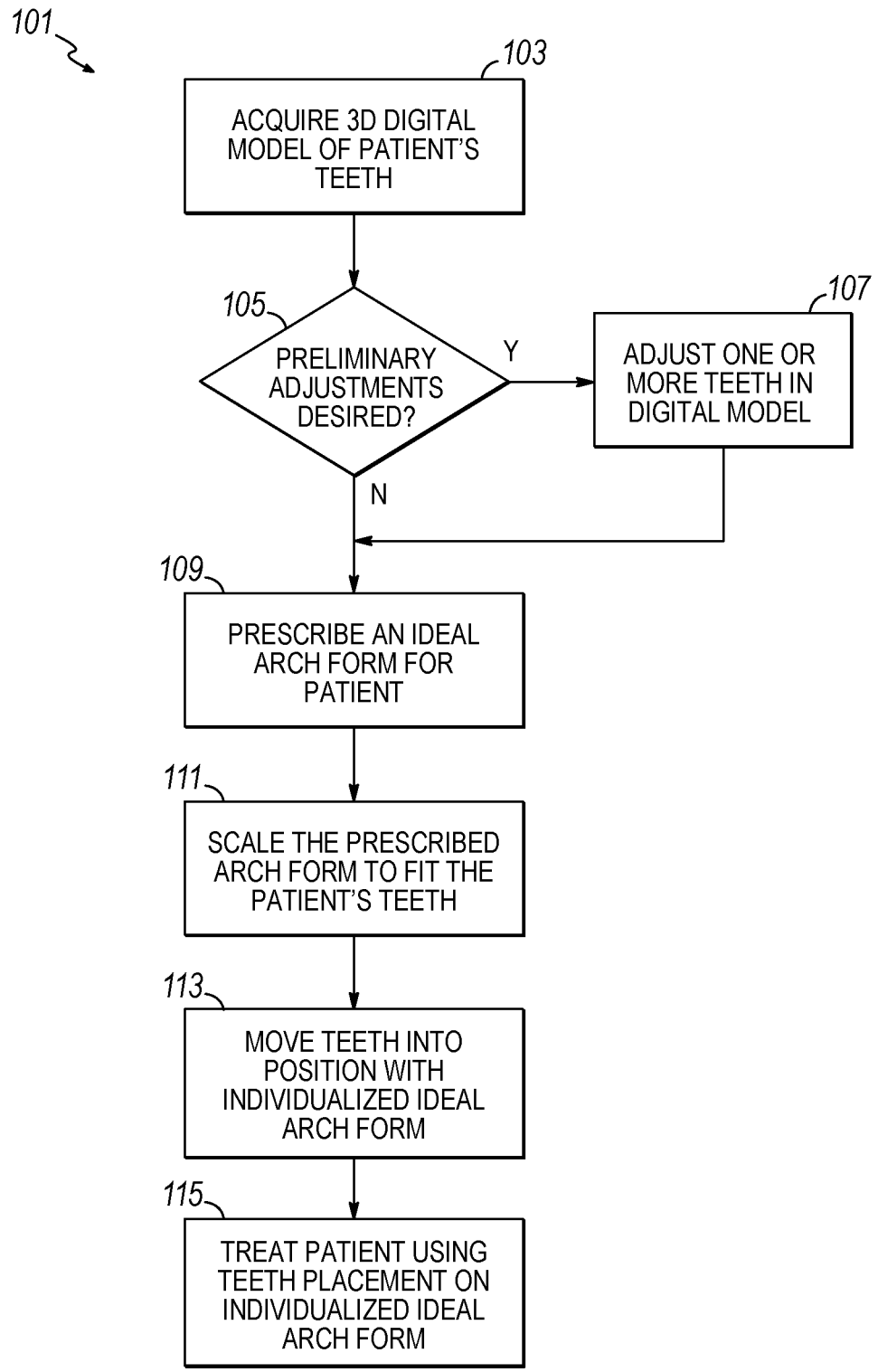
FIG. 9 is a flowchart of a process for use in digital orthodontic setup using a prescribed ideal arch form that may be performed by the imaging system, the orthodontic treatment system, or the orthodontic device production system of FIG. 1.

FIG. 9 illustrates a process 101 for use in digital orthodontic setup using an ideal arch form and in accordance with an embodiment of the present invention. Process 101 begins with a step 103, whereby a digital model of a patient's teeth is acquired, for example by a system similar to imaging system 12 of FIG. 1. In operation, a dental professional may perform an initial assessment of the patient by reviewing the patient's bite and teeth placement. The dental professional thereafter begins to determine a general treatment plan for the patient's teeth and bite to move the teeth from an original position to a final position in accordance with a prescribed setup.

In determining a prescribed setup in accordance with an embodiment of the invention, the dental practitioner reviews and considers a set of digital images of the patient's teeth obtained through imaging system 12. The prescribed setup represents the intended positioning of the teeth after treatment of the patient using the individualized arch form and the repositioning of the teeth with respect to the individualized arch form. The dental practitioner may interface with orthodontic treatment system 14 through display system 16 to observe and consider the images of the patient's teeth.

After acquiring the digital images through imaging system 12, orthodontic treatment system 14 may store these images in raw image database 48. Thereafter, preprocessing module 54 may retrieve and display the set of virtual teeth 62 on display system 16 for review by the dental practitioner.

Thereafter, step 103 proceeds to a step 105. In step 105, a determination is made regarding whether any preliminary or preprocessing adjustments to any of the digital teeth are desired. If it is determined that a preliminary adjustment to at least one digital tooth is desired (the "YES" branch of the decision step), step 105 proceeds to a step 107. If no adjustments are desired (the "NO" branch of the decision step), step 105 proceeds to a step 109.

In step 107, one or more teeth in the digital model are adjusted in accordance with the experiences and clinical judgment of the dental practitioner. The dental practitioner may manipulate one or more reference teeth 63a-63d through interface 64 of display system 16 to set the one or more reference teeth 63a-63d in the preferred three-dimensional space to begin setting up treatment for the patient. For example, the two mandibular first molars may be adjusted to be consistent with the Curve of Wilson. Further, teeth may be oriented in the three-dimensional space to conform to the natural occlusal plane inclination of the patient. The dental practitioner may choose to enforce a perfect symmetry of the arch form by requiring the two mandibular first molars to be adjusted towards the same depth. These adjustments may be manually performed by the dental practitioner or may be part of a proposed automatic algorithm initiated by the dental practitioner. After one or more teeth are adjusted in the digital model, step 107 proceeds to step 109.

In step 109, the dental practitioner selects an ideal arch form for the patient, based on the dental practitioner's experience and clinical judgment. In particular, after the dental practitioner sets each reference tooth 63a-63d, the dental practitioner selects an ideal arch form 71a, 92 from raw arch form database 50 through arch form selection module 56. The selection of ideal arch form 71a, 92 may be performed through interface 64 of display system 16. For example, the dental practitioner may select an ideal arch form similar to arch form 71a shown in FIG. 7 or ideal arch form 92 shown in FIG. 10. Alternatively, an ideal arch form may be automatically selected by an algorithm of the treatment system 14 based on the patient's information made available for processing by the algorithm. The ideal arch form may be stored in a database such as raw arch form database 50 (FIG. 3) or any other mechanism or system for allowing the dental practitioner to select or for allowing the arch form selection module 56 to select and associate a selected ideal arch form with the treatment of the patient. Thereafter, step 109 proceeds to a step 111.

In step 111, the selected ideal arch form is scaled to fit the three-dimensional digital model of the patient's teeth. Once the ideal arch form 71a, 92 is selected by the dental practitioner, arch form scaling module 58 scales the ideal arch form 71a, 92 in accordance with the manipulated reference teeth 63a-63d. For example, this may include automatic scaling of the arch form via the scaling module 58 based on parametric data assigned to particular aspect ratios. In an embodiment of the invention, reference points or landmarks are used to facilitate the proper scaling of the arch form to the virtual model of the patient's teeth. For example, reference points such as branch reference point 72 and central reference point 74 of FIG. 7 may be used to determine the particular aspect ratio of the arch form and scale the arch form 71a, 92 into the customized arch form 71b, 92, described above. Once the ideal arch form is scaled to fit the patient's teeth, step 111 proceeds to a step 113.

In step 113, the remaining teeth are moved into position with the scaled ideal arch form. In an embodiment of the invention, one or more teeth are moved automatically using reference landmarks such as the buccal ridges, whereby each buccal ridge for a particular tooth is aligned to be tangent to the individualized arch form proximate the particular tooth. For example, orthodontic treatment system 14 may automatically align each virtual tooth 62 in accordance with an alignment algorithm. In an embodiment of the invention, the alignment algorithm may use the buccal ridge 78 of each virtual tooth 62, whereby each buccal ridge 78 is aligned to be tangent to the scaled ideal arch form. Further, the alignment algorithm may use the marginal ridge 80 of teeth 62 and align the marginal ridge 80 to be tangent to the scaled ideal arch form. Still further, the alignment algorithm may be configured to keep proper interproximal distances between each tooth 62 when bringing each tooth 62 into alignment with the scaled ideal arch form. By way of additional example only, the dental practitioner may manually manipulate each virtual tooth 62 through interface 64 of display system 16 to align each tooth 62 in accordance with the scaled ideal arch form.

Once each tooth is aligned with the individualized arch form, the teeth are spaced a proper interproximal distance apart to finalize the treatment plan into the prescribed setup for the patient. After each virtual tooth 62 is aligned in accordance with scaled ideal arch form 71b, arch form scaling module 58 stores the aligned teeth 62 in treatment database 52 for further use by the dental practitioner. The aligned teeth 62 represent the prescribed setup and may be transferred to orthodontic device production system 18, whereby a corresponding set of braces, aligners, or another orthodontic treatment device may be manufactured in accordance with the prescribed setup. After the treatment plan is finalized into the prescribed setup, step 113 proceeds to a step 115.

After the prescribed orthodontic device is manufactured, the patient undergoes orthodontic treatment through use of the orthodontic device. In step 115, the patient is treated in accordance with the prescribed setup by applying customized braces or aligners to the patient's teeth to move the teeth, over time, into the position reflected in the prescribed setup. Process 101 ends after step 115.

In general, the routines executed to implement the embodiments of the invention, whether implemented as part of an operating system or a specific application, component, program, object, module or sequence of instructions, or even a subset thereof, may be referred to herein as "computer program code," or simply "program code." Program code typically comprises computer readable instructions that are resident at various times in various memory and storage devices in a computer and that, when read and executed by one or more processors in a computer, cause that computer to execute operations and/or elements embodying the various aspects of the embodiments of the invention. Computer readable program instructions for carrying out operations of the embodiments of the invention may be, for example, assembly language or either source code or object code written in any combination of one or more programming languages.

Various program code described herein may be identified based upon the application within which it is implemented in specific embodiments of the invention. However, it should be appreciated that any particular program nomenclature that follows is used merely for convenience, and thus the invention should not be limited to use solely in any specific application identified and/or implied by such nomenclature. Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The program code embodied in any of the applications/modules described herein is capable of being individually or collectively distributed as a program product in a variety of different forms. In particular, the program code may be distributed using a computer readable storage medium having computer readable program instructions thereon for causing a processor to carry out aspects of the embodiments of the invention.

Computer readable storage media, which is inherently non-transitory, may include volatile and non-volatile and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. A computer readable storage medium should not be construed as transitory signals per se (e.g., radio waves or other propagating electromagnetic waves, electromagnetic waves propagating through a transmission media such as a waveguide, or electrical signals transmitted through a wire). Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts, sequence diagrams, and/or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, and/or operations specified in the flowcharts, sequence diagrams, and/or block diagrams.

In certain alternative embodiments, the functions, acts, and/or operations specified in the flowcharts, sequence diagrams, and/or block diagrams may be re-ordered, processed serially, and/or processed concurrently consistent with embodiments of the invention. Moreover, any of the flowcharts, sequence diagrams, and/or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising".

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A method for making an orthodontic appliance based on a model of a patient's set of teeth, the method comprising:
   receiving an ideal arch form from a raw arch form database of a plurality of unique ideal arch forms, each ideal arch form being of undefined size and including a mid line and unique aspect ratios of width to height at each point along the ideal arch form;
   selecting a reference tooth in the model of the patient's set of teeth;
   measuring a location of the reference tooth in the model;
   calculating an aspect ratio of the reference tooth based on the location;
   identifying coordinates of a reference point on the ideal arch form with the same aspect ratio as the reference tooth;
   scaling the ideal arch form to fit the model of the patient's set of teeth;
   aligning the reference tooth in the model and the reference point of the scaled ideal arch form;
   repositioning at least one other tooth in the model to align the at least one other tooth and the scaled ideal arch form, wherein repositioning the at least one other tooth produces a modified model that defines a prescribed arch form for the patient, the prescribed arch form includes the same unique aspect ratios of width to height as the ideal arch form; and
   transmitting information sufficient to manufacture the orthodontic appliance in accordance with the prescribed arch form.

2. The method of claim 1, wherein scaling the ideal arch form is based on the selected reference tooth.

3. The method of claim 2, wherein scaling includes resizing the ideal arch form based on the coordinates of the reference point.

4. The method of claim 1, wherein measuring includes measuring a width and a height of the reference tooth location in the model of the set of teeth.

5. The method of claim 1, further comprising:
repositioning the reference tooth in the model prior to scaling the selected arch form.

6. The method of claim 1, wherein repositioning includes aligning a buccal ridge of the at least one other tooth with the scaled ideal arch form.

7. The method of claim 6, wherein the buccal ridge is aligned to be tangent to the scaled ideal arch form.

8. The method of claim 1, wherein the ideal arch form is configured to be computationally evaluated at any given point along its length.

9. The method of claim 1, wherein the ideal arch form is represented by a closed-form mathematical formulation.

10. The method of claim 1, wherein the ideal arch form is defined by unique aspect ratios along the arch form.

11. The method of claim 1, wherein selecting from the raw arch form database is based on one or more patient characteristics.

12. The method of claim 1, further comprising:
after transmitting, manufacturing the orthodontic appliance in accordance with the prescribed arch form for use by the patient in accordance with an orthodontic treatment plan.

13. A system for digital orthodontic setup from a digital model of a patient's teeth, the system comprising:
a processor; and
a memory being coupled to the processor and including instructions that, when executed by the processor, cause the system to:
receive an ideal arch form for the digital model of the patient's teeth from a database of a plurality of unique ideal arch forms, each ideal arch form being of undefined size and including a mid line and unique aspect ratios of width to height at each point along the ideal arch form;
select a reference tooth in the model of the patient's set of teeth;
measure a location of the reference tooth in the model;
calculate an aspect ratio of the reference tooth based on the location;
identify coordinates of a reference point on the ideal arch form with the same aspect ratio as the reference tooth;
scale the arch form to fit the digital model;
align the reference tooth in the digital model and the reference point of the scaled ideal arch form;
reposition at least one other tooth in the digital model to align the at least one other tooth and the scaled ideal arch form, wherein when repositioned, the at least one other tooth produces a modified model that defines a prescribed arch form for the patient, the prescribed arch form includes the same unique aspect ratios of width to height along the prescribed arch form as the ideal arch form; and
prepare information in accordance with the prescribed arch form to have an orthodontic appliance manufactured for treatment of the patient.

14. The system of claim 13, wherein the scale of the selected arch form is based at least in part on the reference tooth in the digital model.

15. The system of claim 13, wherein the memory includes instructions that, when executed by the processor, cause the system to reposition at least one other tooth in the digital model so as to have at least one of a buccal ridge or a marginal ridge of the at least one other tooth to be tangent to the scaled ideal arch form.

16. The system of claim 13, further comprising:
an orthodontic device production system capable of manufacturing the orthodontic appliance in accordance with the prescribed arch form for use by the patient in accordance with an orthodontic treatment plan.

17. A computer program product useable to treat teeth of a patient comprising:
a non-transitory computer-readable storage medium; and
instructions stored on the non-transitory computer-readable storage medium that, when executed by a processor, cause the processor to:
receive an ideal arch form from a database of a plurality of unique ideal arch forms, each ideal arch form being of undefined size and including a mid line and unique aspect ratios of width to height at each point along the ideal arch form;
select a reference tooth in the model of the patient's set of teeth;
measure a location of the reference tooth in the model;
calculate an aspect ratio of the reference tooth based on the location;
identify coordinates of a reference point on the ideal arch form with the same aspect ratio as the reference tooth;
scale the arch form to fit a digital model of the patient's teeth;
align at least one the reference tooth in the digital model and the reference point of the scaled ideal arch form;
reposition at least one other tooth in the digital model to align the at least one other tooth and the scaled ideal arch form, wherein when repositioned, the at least one other tooth produces a modified model that defines a prescribed arch form for the patient, the prescribed arch form includes the same unique aspect ratios of width to height along the prescribed arch form as the ideal arch form; and
prepare information in accordance with the prescribed arch form to have an orthodontic appliance manufactured for treatment of the patient.

* * * * *